United States Patent [19]
Tensmeyer

[11] 3,947,415
[45] Mar. 30, 1976

[54] CEFAMANDOLE DERIVATIVES
[75] Inventor: Lowell G. Tensmeyer, Indianapolis, Ind.
[73] Assignee: Eli Lilly and Company, Indianapolis, Ind.
[22] Filed: Dec. 23, 1974
[21] Appl. No.: 535,235

[52] U.S. Cl.............................. 260/243 C; 424/246
[51] Int. Cl.² ...................................... C07D 501/20
[58] Field of Search ................................. 260/243 C

[56] References Cited
UNITED STATES PATENTS
3,840,531   10/1974   Greene............................ 260/243 C

*Primary Examiner*—Nicholas S. Rizzo
*Attorney, Agent, or Firm*—William C. Martens, Jr.; Everet F. Smith

[57] ABSTRACT

A novel crystalline derivative comprising the sodium salt of cefamandole and L(−) ethyl lactate is herein defined. This derivative can be used to purify impure amorphous cefamandole sodium by the steps of preparing the crystalline derivative, isolating it from the mixture, and regenerating cefamandole sodium therefrom.

7 Claims, No Drawings

CEFAMANDOLE DERIVATIVES

BACKGROUND OF THE INVENTION

Cefamandole is a generic term used to identify a chemical compound, 7-(D-α-hydroxyphenylacetamido)-3-(1-methyl-1H-tetrazol-5-ylthio)-methyl-3-cephem-4-carboxylic acid, having the formula

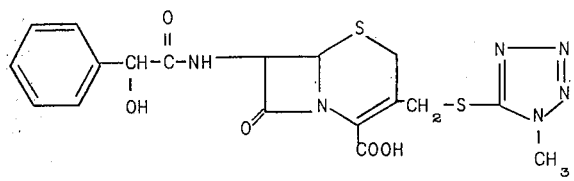

This compound is active as a broad spectrum antibiotic effective in controlling diseases caused by a wide variety of Gram-positive and Gram-negative microorganisms.

Cefamandole is one of the semi-synthetically produced cephalosporins. It can be prepared, for example, by treating 7-aminocephalosporanic acid, commonly known as 7-ACA, suitably protected in the 7-position, for example, by a formyl group, with 1-methyl-1H-tetrazole-5-thiol, or an alkali metal, alkaline earth metal, or ammonium salt thereof, to produce the corresponding 7-formamido-3-(1-methyl-1H-tetrazol-5-ylthio)-methyl-3-cephem-4-carboxylic acid. This product then can be cleaved in accordance with known techniques to produce the corresponding 7-amino-3-(1-methyl-1H-tetrazol-5-ylthio)methyl-3-cephem-4-carboxylic acid, and the resulting cleaved product then can be acylated, for example, employing anhydro-O-carboxymandelic acid, to produce the desired cefamandole. The aforementioned sequence is typical of several methods which are available in the preparation of cefamandole. For example, the aforementioned acylation step can be carried out employing a mixed anhydride form of D-mandelic acid in which the hydroxyl group has been protected by a suitable blocking group, for example, a formyl or an acetyl group. The mixed anhydride then can be used as acylating agent for the 7-aminocephalosporin compound to form the hydroxy-protected cefamandole which then is cleaved to produce the desired cefamandole product. Alternative methods for effecting acylation of the 7-amino group are well known to those of ordinary skill in the art.

The source of the 7-formamido derivative of 7-ACA employed in the foregoing sequence is 7-ACA itself, and the latter can be obtained from cephalosporin C, more precisely known as 7-(5-aminoadipamido)cephalosporanic acid, which can be prepared by cultivating a cephalosporin C-producing organism in a suitable nutrient medium. The cephalosporin C can then be readily converted to the corresponding nucleus compound, 7-ACA, by cleaving the 5-aminoadipamyl side chain by known procedures.

A highly preferred form of cefamandole is its sodium salt derivative which has the following formula:

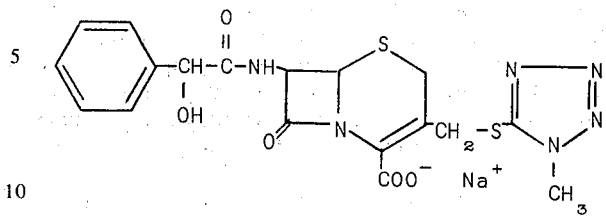

This form of cefamandole, however, does not exist in crystalline form, or at least a crystalline form has not as yet been discovered. As a result of this fact, two deficiencies have been noted. First, cefamandole sodium has been found to be purifiable to the extent necessary for administration only by very difficult and cumbersome techniques. Secondly, amorphous cefamandole sodium does not exhibit the degree of stability that one would desire, and certainly not such as one would expect from a corresponding crystalline structure.

In this context, therefore, it has become desirable to develop a crystalline form of cefamandole sodium, which form would be useful in purifying cefamandole sodium itself. This purification sequence then would comprise preparation of a crystalline derivative of cefamandole sodium from an impure or relatively impure lot of cefamandole sodium. The crystalline derivative then could be isolated from the impure mixture leaving impurities behind. Any such desirable crystalline derivative then would be usable as such or would exhibit properties which would permit its ready decomposition with regeneration of cefamandole sodium itself in purified form.

Such a derivative would permit purification of impure amorphous cefamandole sodium; additionally, it would permit the retention of cefamandole sodium in a highly stable form, which form could be decomposed with regeneration of the cefamandole sodium at some point prior to packaging of the cefamandole sodium in a unit suitable for ultimate administration.

Such a discovery forms the basis of this invention. It is an object, therefore, of this invention to provide a novel composition of matter comprising a stable, crystalline derivative of cefamandole sodium.

It is a further object of this invention to provide a method for purifying cefamandole sodium by preparing and recovering a defined crystalline derivative thereof and subsequently decomposing the derivative to recover cefamandole sodium itself.

SUMMARY OF THE INVENTION

Thus, one aspect of this invention is a crystalline composition of matter comprising a complex of the sodium salt of cefamandole and L(−) ethyl lactate.

In another aspect of this invention there is provided a process for purifying the sodium salt of cefamandole which comprises converting said salt containing impurities to a crystalline complex comprising cefamandole sodium and L(−) ethyl lactate, separating said crystalline complex from said impurities, and decomposing said crystalline complex to recover purified cefamandole sodium.

DETAILED DESCRIPTION OF THE INVENTION

As indicated hereinabove, this invention relates to a novel composition of matter as well as to a process for purifying the sodium salt of cefamandole.

The novel composition of matter of this invention comprises cefamandole sodium and L(—) ethyl lactate. The ratio on a molar basis of the L(—) ethyl lactate to the cefamandole sodium present in the composition of this invention is 1:1. As will be developed in more depth hereinafter, the novel composition of matter of this invention can be prepared from the dl-ethyl lactate racemic mixture or from the optically active L(—) ethyl lactate.

The novel crystalline form provided by this invention has the following unique X-ray powder diffraction characteristics at λ = 1.5405 using a Cu:Ni 45 kv. 20 ma. source.

| spacing d | Relative intersities I/I₁ |
|---|---|
| 15.20 | 1.00 |
| 9.40 | .50 |
| 8.75 | .10 |
| 7.39 | .15 |
| 5.86 | .20 |
| 5.60 | .40 |
| 5.37 | .15 |
| 4.81 | 1.00 |
| 4.37 | .80 |
| 3.93 | .90 |
| 3.72 | 1.00 |
| 3.42 | .20 |
| 3.18 | .50 |
| 3.03 | .05 |
| 2.93 | .30 |
| 2.84 | .20 |
| 2.71 | .10 |
| 2.53 | .02 |
| 2.49 | .05 |
| 2.38 | .05 |
| 2.25 | .02 |
| 2.19 | .05 |
| 2.01 | .05 |
| 1.87 | .05 |

The above X-ray powder diffraction pattern is representative of the aforedescribed composition whether it has been prepared from the dl-ethyl lactate racemic mixture or whether its source is the optically active L(—) ethyl acetate.

The process aspect of this invention provides a method for purification of the sodium salt of cefamandole by the sequence of preparing the novel crystalline complex of this invention, separating the crystalline complex from the preparation medium, and decomposing the crystalline complex to regenerate the sodium salt of cefamandole in purified form.

It has been discovered that the sodium salt of cefamandole combines exclusively with the L(—) optical isomer of ethyl lactate. Thus, L(—) ethyl lactate, of course, can itself be employed in preparation of the crystalline complex of this invention. However, the racemic mixture, dl-ethyl lactate, can also be employed since it has been discovered that the cefamandole sodium, in effect, functions as a resolving agent, selectively reacting with the L(—) ethyl lactate which is present in the racemic mixture and excluding the D(+) ethyl lactate.

Depending upon the conditions employed in the initial preparation of the crystalline complex of this invention, the preparation can be quite rapid, being completed in a matter of a few hours, or it can take an extended period of time, sometimes up to several days. However, once an initial preparation of the complex has been accomplished, the time required for subsequent preparations can be substantially reduced merely by the availability of crystals from the first preparation, which crystals can be employed to seed the medium in subsequent preparations. An important factor in determining the length of preparation time is the concentration of the solution in which the complex is generated and from which it is isolated. As a minimum, the solution must be saturated. However, it is preferred that the preparation be carried out at supersaturated conditions since the preparation time, even without seeding, is generally inversely dependent upon the degree of concentration beyond saturation.

Preparation of the crystalline complex of this invention is accomplished by dissolving the sodium salt of cefamandole in L(—) or dl-ethyl lactate in an amount sufficient to produce at least a saturated solution thereof. Solubility of the amorphous sodium salt of cefamandole in ethyl lactate is about 200–350 mg./ml. at room temperature. Dissolution can be encouraged by any of several techniques, including stirring, mechanical shaking, ultrasonification, moderate warming to about 30°C., and the like. Upon completion of solution, the mixture is maintained at a temperature of from about —20°C. to about +30°C. for a time sufficient to produce crystallization of the crystalline complex of this invention. Preferably, the mixture is maintained at a temperature of from about —10°C. to about +10°C. The solubility of the complex in ethyl lactate appears to be relatively independent of temperature. However, it is advisable to maintain the crystallizating solution at the lower portion of the temperature range to minimize decomposition of the cefamandole. As indicated hereinabove, the time for crystallization can be greatly reduced by incorporating into the saturated or supersaturated solution seeds of the crystalline complex obtained from a previous preparation or by carrying out the preparation under greatly supersaturated conditions.

After the solution has been maintained at the requisite temperature for a period sufficient to accomplish the extent of crystal growth which is desired, the crystals can be harvested from the mixture by filtration. Residual amounts of the mother liquor, containing undesirable impurities, can be removed from the harvested crystals by washing the crystals with cold (about —5°C. to about +5°C.) ethyl lactate or with ethyl ether, the latter being a non-solvent of the crystalline complex, or with a mixture of ethyl lactate and ethyl ether. Other non-polar solvents can be employed; those which have a high vapor pressure are especially preferred since they are easily removable by drying.

The resulting crystals then can be stored at room temperature or below for extended periods with little or no decomposition. Alternatively, the crystals can be decomposed to regenerate the cefamandole sodium in purified form.

Decomposition of the crystalline complex with regeneration of cefamandole sodium can be accomplished by placing the crystals in an excess of ethanol. The ethanol apparently preferentially extracts the ethyl lactate from the complex leaving a purified amorphous sodium salt of cefamandole. The desired purified amorphous sodium salt of cefamandole can be recovered by filtration and washed with water to remove residual amounts of ethanol and ethyl lactate. Methanol, since it dissolves both the cefamandole and the ethyl lactate, is not a particularly useful regenerating solvent. However, those solvents which have a polarity similar to ethanol, such as, for example, isopropyl alcohol, methyl acetate, and the like, are useful to release the ethyl lactate from the complex with regeneration and recovery of the amorphous cefamandole. Ethanol, however, is the preferred regenerating solvent.

The resulting amorphous sodium salt of cefamandole is pure and ready for use as an active anti-bacterial agent.

The following examples are provided to illustrate the teaching of this invention. They are not intended to be limiting upon the general scope thereof.

EXAMPLE 1 — Crystalline Complex Prepared from L(−) Ethyl Lactate.

To 5.00 ml. of L(−)ethyl lactate were added 1.7 g. of the sodium salt of cefamandole. Most of the sodium cefamandole dissolved readily; however, to facilitate complete dissolution, the mixture was subjected to ultrasonification. Within minutes after solution was effected, the mixture became cloudy and then became too viscous to be poured. Microscopic examination of the white mass showed extremely large numbers of very tiny needles. No amorphous material could be seen. Since the mass was too viscous to handle and the crystals were too small to use, an additional 0.5 ml. of L(−)ethyl lactate was added, and the mixture was maintained overnight at about 2°C. Examination of the mixture indicated no discernible change; however, the mass no longer was so viscous as to be cream-like in consistency.

The mixture was maintained for an additional day, and then was filtered. Filtration was carried out using a small glass frit funnel. The funnel was filled with the mixture, and vacuum then was applied with removal of the mother liquor from the mixture. The resulting mass of crystals which was collected was washed twice with cold dl-ethyl lactate and then with ethyl ether. Ethyl ether served well as a non-solvent, and the crystals were washed five or six times with ethyl ether by the sequence of discontinuing the vacuum suction, adding ethyl ether, stirring the crystals suspended in ethyl ether, and removing the ether by vacuum suction. The ultimate resultant mass was air-dried and stored as a white, free-flowing crystalline material.

An nmr analysis in $D_2O$ indicated the product to be a 1:1 complex of ethyl lactate and sodium cefamandole. The X-ray powder pattern is identical with that provided hereinabove.

EXAMPLE 2 — Crystalline Complex Prepared from d,l-Ethyl Lactate.

To 5.00 ml. of dl-ethyl lactate were added 1.30 g. of the sodium salt of cephamandole. The solid material wetted readily and began dissolving rapidly. Ultrasonification was employed toward the end of dissolution; however, residual amounts of amorphous sodium cefamandole did not dissolve. Microscopic examination of the mixture showed the liquid to contain many small amorphous particles in suspension. The mixture was maintained at room temperature. Microscopic examination of the mixture after about 3–4 hours showed crystals beginning to form. The rate of crystal formation from the d,l-ethyl lactate was considerably slower than from the L(−) ethyl lactate of Example 1. A microscopic examination after an additional period of time indicated an increasing number of crystals with accompanying cloudiness of the solution. All amorphous material was gone. After another period of time, the liquid had turned to a somewhat viscous mass. Microscopic examination showed the presence of two crystalline habits. One of the habits was needle-like crystals, either singly or in groups, whereas the other was a more 2-dimensional plate, greater in length than width but substantially wider than the needle-like crystals.

The mixture was stored overnight at about 2°C. The mixture then was prepared for filtering and was filtered in accordance with the technique employed in Example 1.

The resulting dry, free-flowing crystals were shown by nmr analysis to contain a 1:1 ratio of ethyl lactate and sodium cefamandole. The X-ray powder pattern of this substance was identical in all respects to that described hereinabove and to the product from Example 1. From this information it is evident that the L(−) ethyl lactate compound of the dl mixture is the active component in forming the crystalline complex of this invention.

EXAMPLE 3 — Crystalline Complex Prepared in Large Scale

To 125 ml. of d,l-ethyl lactate were added 32.5 g. of sodium salt of cefamandole. The mixture, maintained at room temperature, was shaken and periodically subjected to ultrasonification over 3–4 hours. At the end of this time, amorphous material still remained undissolved, and there was indication that some crystallization was beginning. The mixture then was maintained at 11.5°C. for 3 days.

At the end of this period, large amounts of crystalline material were present; however, some amorphous material was also visible. The mixture was sonified and then was placed on a mechanical shaker. The temperature rose rapidly to 35°C. with apparent dissolution of all amorphous material; however, a mercaptan-like odor was evident.

A sample for microscopic analysis was removed, and the mixture then was cooled to 11.5°C. Microscopic analysis of the sample indicated excellent crystalline material and the absence of amorphous material. The mixture was maintained at 11.5°C. for several hours and then was cooled to −6°C. and maintained at this temperature for about 2 days.

The crystals were harvested using a 60 ml. frit suction funnel. The crystals were filtered under suction to separate the mother liquor. The crystals then were washed twice with 15 ml. of portions of cold d,l-ethyl lactate. The crystals then were washed clear of ethyl lactate using four 30 ml. portions of ethyl ether. The product, a crystalline complex of L(−) ethyl lactate and sodium cefamandole, was dried by pulling air through the crystalline mass.

EXAMPLE 4 — Regeneration of Cefamandole Sodium

To 5 ml. of ethanol are added 100 mg. of the crystalline complex of L(−) ethyl lactate and sodium cefamandole. The mixture is shaken at room temperature for about 10 minutes. The resulting mixture then is filtered to obtain a highly pure, amorphous cefamandole sodium.

I claim:

1. A crystalline complex comprising the sodium salt of cefamandole and L(−) ethyl lactate.

2. Process for purifying the sodium salt of cefamandole, which comprises converting said salt containing impurities to the crystalline complex of cefamandole sodium and L(−) ethyl lactate, separating said crystalline complex from said impurities, and decomposing said crystalline complex to recover purified cefamandole sodium.

3. Process of claim 2, in which the crystalline complex is prepared from at least a saturated solution of the sodium salt of cefamandole in a d,l-ethyl lactate racemic mixture.

4. Process of claim 2, in which the crystalline complex is prepared from at least a saturated solution of the sodium salt of cefamandole in L(−) ethyl lactate.

5. Process of claim 3, in which the solution is maintained at a temperature of from about −20°C. to about +30°C. for a time sufficient to produce crystallization of the crystalline complex.

6. Process of claim 2, in which the crystalline complex is decomposed to the sodium salt of cefamandole by adding the separated crystals to an excess of ethanol and filtering the resulting mixture.

7. Process of claim 4, in which the solution is maintained at a temperature of from about −20°C. to about +30°C. for a time sufficient to produce crystallization of the crystalline complex.

* * * * *